US010990719B2

(12) United States Patent
Lee

(10) Patent No.: US 10,990,719 B2
(45) Date of Patent: *Apr. 27, 2021

(54) ASSIMILATING A SOIL SAMPLE INTO A DIGITAL NUTRIENT MODEL

(71) Applicant: The Climate Corporation, San Francisco, CA (US)

(72) Inventor: Wayne Tai Lee, San Francisco, CA (US)

(73) Assignee: The Climate Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,860

(22) Filed: Apr. 30, 2019

(65) Prior Publication Data

US 2019/0258760 A1 Aug. 22, 2019

Related U.S. Application Data

(63) Continuation of application No. 15/140,378, filed on Apr. 27, 2016, now Pat. No. 10,275,550.

(51) Int. Cl.
*G06F 3/00* (2006.01)
*G06F 30/20* (2020.01)
(Continued)

(52) U.S. Cl.
CPC .............. *G06F 30/20* (2020.01); *G16B 15/00* (2019.02); *G01N 2033/245* (2013.01)

(58) Field of Classification Search
CPC .................................................. G06F 17/5009
(Continued)

(56) References Cited

U.S. PATENT DOCUMENTS 5,468,088 A  11/1995 Shoemaker et al.
5,668,719 A   9/1997 Bobrov et al.
(Continued)

FOREIGN PATENT DOCUMENTS

EP   2 196 085 A2   6/2010
EP   2196085 A2     6/2010
(Continued)

OTHER PUBLICATIONS

Christian Folberth, Uncertainty in soil data can outweigh climate impact signals in global crop yield simulations. (Year: 2016).*
(Continued)

*Primary Examiner* — Lechi Truong
(74) *Attorney, Agent, or Firm* — Hickman Becker Bingham Ledesma LLP

(57) ABSTRACT

In an embodiment, agricultural intelligence computer system stores a digital model of nutrient content in soil which includes a plurality of values and expressions that define transformations of or relationships between the values and produce estimates of nutrient content values in soil. The agricultural intelligence computer receives nutrient content measurement values for a particular field at a particular time. The agricultural intelligence computer system uses the digital model of nutrient content to compute a nutrient content value for the particular field at the particular time. The agricultural intelligence computer system identifies a modeling uncertainty corresponding to the computed nutrient content value and a measurement uncertainty corresponding to the received measurement values. Based on the identified uncertainties, the modeled nutrient content value, and the received measurement values, the agricultural intelligence computer system computes an assimilated nutrient content value.

19 Claims, 8 Drawing Sheets

(51) Int. Cl.
*G16B 15/00* (2019.01)
*G01N 33/24* (2006.01)

(58) Field of Classification Search
USPC .......................................................... 703/6
See application file for complete search history.

(56) References Cited

U.S. PATENT DOCUMENTS

| | | | |
|---|---|---|---|
| 6,535,817 B1 | 3/2003 | Krishnamurti | |
| 6,810,368 B1 | 10/2004 | Pednault | |
| 6,874,707 B2 | 4/2005 | Skinner | |
| 7,171,912 B2 | 2/2007 | Fraisse | |
| 9,107,341 B2 | 8/2015 | Martinez | |
| 9,519,861 B1 | 12/2016 | Gates | |
| 2004/0064255 A1 | 4/2004 | Egi | |
| 2005/0234691 A1 | 10/2005 | Singh et al. | |
| 2006/0254371 A1 | 11/2006 | Shiloni | |
| 2007/0039745 A1 | 2/2007 | Anderson | |
| 2007/0260400 A1 | 11/2007 | Morag | |
| 2010/0024296 A1 | 2/2010 | Lazarus | |
| 2010/0040281 A1* | 2/2010 | Chen | G06K 9/6229 382/156 |
| 2010/0332039 A1 | 12/2010 | Danieli | |
| 2012/0083907 A1 | 4/2012 | Motavalli et al. | |
| 2012/0101861 A1 | 4/2012 | Lindores | |
| 2012/0109614 A1 | 5/2012 | Lindores | |
| 2012/0237083 A1* | 9/2012 | Lange | G06K 9/00805 382/103 |
| 2013/0144827 A1 | 6/2013 | Trevino | |
| 2013/0332205 A1 | 12/2013 | Friedberg | |
| 2014/0012732 A1 | 1/2014 | Lindores | |
| 2014/0067745 A1 | 3/2014 | Avey | |
| 2014/0165713 A1 | 6/2014 | Frey | |
| 2015/0026023 A1 | 1/2015 | Sirota et al. | |
| 2015/0254800 A1 | 9/2015 | Johnson | |
| 2016/0232621 A1 | 8/2016 | Ethington et al. | |
| 2017/0061052 A1 | 3/2017 | Gates | |
| 2017/0165713 A1 | 6/2017 | Frey | |
| 2017/0316124 A1 | 11/2017 | Lee | |
| 2020/0151376 A1 | 5/2020 | Gates | |

FOREIGN PATENT DOCUMENTS

| EP | 2 244 108 A2 | 10/2010 |
|---|---|---|
| WO | WO 2015/051339 A1 | 4/2015 |
| WO | WO 2016/127094 A1 | 8/2016 |

OTHER PUBLICATIONS

U.S. Appl. No. 14/842,321, filed Sep. 1, 2015, Interview Summary, dated Apr. 5, 2016.
U.S. Appl. No. 14/842,321, filed Sep. 1, 2015, Office Action, dated Jan. 29, 2016.
U.S. Appl. No. 14/842,321, filed Sep. 1, 2015, Notice of Allowance, dated Aug. 26, 2016.
U.S. Appl. No. 14/842,321, filed Sep. 1, 2015, Interview Summary, dated Jun. 16, 2016.
U.S. Appl. No. 14/842,321, filed Sep. 1, 2015, Advisory Action, dated Jul. 28, 2016.
U.S. Appl. No. 14/842,231, filed Sep. 1, 2015, Final Office Action, dated May 26, 2016.
Lee, U.S. Appl. No. 15/140,378, filed Apr. 27, 2016, Office Action, dated May 17, 2018.
Lee, U.S. Appl. No. 15/140,378, filed Apr. 27, 2016, Notice of Allowance, dated Dec. 13, 2018.
Lee, U.S. Appl. No. 15/140,378, filed Apr. 27, 2016, Final Office Action, dated Sep. 20, 2018.
Lee, U.S. Appl. No. 15/140,378, filed Apr. 27, 2016, Corrected Notice of Allowability, dated Jan. 24, 2019.
European Claims in application No. PCT/US2016/016838, dated May 2016, 5 pages.
Gneiting et al, "Probabilistic Forecasting", Annual Reviews Further, The Annual Review of Statistics and Its Application is online at statistics.annualreviews.org, dated 2014, 30 pages.
European Patent Office, "Search Report" in application No. PCT/US2016/029385, dated Jul. 28, 2016, 12 pages.
European Patent Office, "Search Report" in application No. PCT/US2016/023348, dated May 30, 2016, 13 pages.
European Patent Office, "Search Report" in application No. PCT/US2016/022503, dated May 2, 2016, 12 pages.
European Patent Office, "Search Report" in application No. PCT/US2016/016838, dated May 17, 2016, 14 pages.
European Patent Office, "Search Report" in application No. PCT/US2015/049486, dated Nov. 12, 2015, 9 pages.
European Claims in application No. PCT/US2016/029385, dated Jul. 2016, 11 pages.
Ahmad et al., "Estimating Soil Moisture Using Remote Sensing Data: A Machine Learning Approach", Advances in Water Resources, 33.1 dated 2010, pp. 69-80.
European Claims in application No. PCT/US2016/022503, dated May 2016, 7 pages.
Gneiting et al., "Comparing Density Forecasts Using Threshold- and Quantile-Weighted Scoring Rules", Taylor & Francis Informa Ltd, dated Aug. 19, 2015, 13 pages.
European Claims in application No. PCT/US2015/049486, dated Nov. 2015, 6 pages.
Dutton et al., "Calibration and combination of dynamical seasonal forecasts to enhance the value of predicted probabilities for managing risk",Springer-Verlag Berlin Heidelberg, dated 2013, 17 pages.
Current Claims in application No. PCT/US2017/028689, dated Oct. 2018, 7 pages.
Current Claims in application No. PCT/US2016/029385, dated Jan. 2018, 11 pages.
Current Claims in application No. PCT/US 17/28689, dated Jul. 2017, 7 pages.
Clark et al., "The Schaake Shuffle: A Method for Reconstructing Space-Time Variability in Forecasted Precipitation and Temperature Fields", dated February 2004, American Meteorological Society 20 pgs.
Berrocal et al., "Combining Spatial Statistical and Ensemble Information in Probabilistic Weather Forecasts", Monthly Weather Review, vol. 135, dated 2007 American Meteorological Society, 17 pages.
American Meteorological Society, "Bulletin of the American Meteorological Society", Early Online Release, dated 2013 American Meteorological Society, 47 pages.
European Claims in application No. PCT/US2016/023348, dated May 2016, 6 pages.
Sattari et al., "Crop Yield Response to Soil Fertility and N, P, K Inouts in Different Environments: Testing and Improving the QUEFTS Model", Field Crops Research 157, dated 2014 pp. 35-46.
Veenhuis, Bruce, "Spread Calibration of Ensemble MOS Forecasts", dated Jul. 2013, 16 pages.
Van Arkel et al., "Identifying Sampling Locations for Field-Scale Soil Moisture Estimation Using K-Means Clustering", Water Resources Research, 50.8, dated 2014, pp. 7050-7057.
Thorarinsdottir et al., "Probabilistic forecasts of wind speed: ensemble model output statistics by using heteroscedastic censored regression", Universitat Heidelberg, Germany, dated Jun. 2009, 18 pages.
The International Bureau of WIPO, "International Preliminary Report on Patentability", in application No. PCT/US2017/028689, dated Oct. 30, 2018, 6.
The International Bureau of WIPO, "International Preliminary Report on Patentability", in application No. PCT/US2016/029385, dated Jan. 16, 2018, 7.
Taylor, DL, "Innovation in the Fields" The Salinas Californian, dated Oct. 19, 2013.
Sloughter et al., "Probabilistic Quantitative Precipitation Forecasting Using Bayesian Model Averaging", dated Sep. 2007 American Meteorological Society, 12 pages.
Scheuerer, M., "Probabilistic quantitative precipitation forecasting using Ensemble Model Output Statistics", Quarterly Journal of the RoyalMeteorological Society, dated Apr. 17, 2013, 11 pages.

(56) References Cited

OTHER PUBLICATIONS

Gneiting et al,., "Strictly Proper Scoring Rules, Prediction, and Estimation", 2007 Journal of the American Statistical Association, dated Mar. 2007, vol. 102, No. 477, Review Article, 20 pages.
Schefzik et al., "Uncertainty Quantification in Complex Simulation Models Using Ensemble Copula Coupling",Statistical Science, dated 2013, vol. 28, No. 4, 25 pages.
Gneiting et al., "Assessing probabilistic forecasts of multivariate quantities, with an application to ensemble predictions of surface winds", dated Jun. 2008, 26 pages.
Raf Tery et al ., "Using Bayesian Model Averaging to Calibrate Forecast Ensembles", dated May 2005 American Meteorological Society, 20 pages.
Negm et al., "Drainmod-DSSAT Model for Simulating Hydrology, Soil Carbon and Nitrogen Dynamics, and Crop Growth for Drained Crop Land", Agricultural Water Management 137 dated 2014, 45 pgs.
Luc Feyen, Parameter Optimisation and Uncertainty Assessment for Large-Scale Streamflow Simulation with the LISFLOOD Model, dated 2005, 14 pages.
Johnson et al., "Medium-range multimodel ensemble combination and calibration", Quarterly Journal of the Royal Meteorological Society,Published online Mar. 9, 2009 in Wiley InterScience, 18 pages.
International Searching Authority, "Search Report" in application No. PCT/US17/28689, dated Jul. 24, 2017, 9 pages.
Ines et al., "Inverse Modeling in Estimating Soil Hydraulic Functions: A Genetic Algorith, Approach", Hydrology and Earth Systems Sciences Discussions, 6.1 dated 2002, pp. 49-66.
Granlund et al., "Estimation of the Impact of Fertilisation Rate on Nitrate Leaching in Finland Using a Mathematical Simulation Model", Agriculture, Ecosystem and Environment 80.1, dated 2002, 13 pgs.

Vrugt et al., "Ensemble Bayesian model averaging using Markov Chain Monte Carlo sampling", Springer Science+Business Media B.V. 2008, Received: Jun. 7, 2008 / Accepted: Sep. 25, 2008, 17 pages.
Scheuerer et al., "Spatially adaptive post-processing of ensemble forecasts for temperature", dated Feb. 6, 2013, 17 pages.
Gates, U.S. Appl. No. 15/351,344, filed Nov. 14, 2019, Notice of Allowance, dated Sep. 4, 2019.
European Patent Office, "Search Report" in application No. 17790143.6-1224, dated Nov. 25, 2019, 11 pages.
European Claims in application No. 17790143.6-1224, dated Nov. 2019, 7 pages.
B. Basso et al., "Spatial Validation of Crop Models for Precision Agriculture", Agricultural Systems, vol. 68, No. 2, dated May 1, 2001, pp. 97-112.
Australian Patent Office, "Search Report" in application No. 2016294138, dated Jan. 28, 2020, 4 pages.
Australian Claims in application No. 2016294138, dated Jan. 2020, 11 pages.
Henderson, Gary, "Verification of Long-Term Pavement Performance Virtual Weather Stations Phase I Report-Accuracy and Reliability of Virtual Weather Stations", dated May 2006, 93 pages.
Gates, U.S. Appl. No. 15/351,344, filed Nov. 17, 2016, Office Action, dated May 13, 2020.
Gates, U.S. Appl. No. 15/351,344, filed Nov. 14, 2016, Final Office Action, dated Sep. 28, 2020.
Argentina Patent Office, "Search Report" in application No. 20150102912, dated Aug. 11, 2020, 3 pages.
Argentina claims in application No. 20150102912, dated Aug. 2020, 5 pages.

\* cited by examiner (a)

ASSIMILATING A SOIL SAMPLE INTO A DIGITAL NUTRIENT MODEL

BENEFIT CLAIM

This application claims the benefit under 35 U.S.C. § 120 as a Continuation of application Ser. No. 15/140,378, filed Apr. 27, 2016, now U.S. Pat. No. 10,275,550, the entire contents of which is hereby incorporated by reference for all purposes as if fully set forth herein. The applicants hereby rescind any disclaimer of claim scope in the parent applications or the prosecution history thereof and advise the USPTO that the claims in this application may be broader than any claim in the parent applications.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015 The Climate Corporation.

FIELD OF THE DISCLOSURE

The present disclosure relates to digital computer modeling of nutrients in a field, such as nitrogen, phosphorus, and potassium. Additionally, the present disclosure relates to techniques for improving an estimation of nutrient content by assimilating data from a soil sample.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Nutrients are essential in the growth and development of crops. Crops absorb nutrients such as nitrogen, phosphorus, and potassium in the surrounding soil to facilitate crop growth. Different types of crops have different requirements for each nutrient. When a crop is unable to meet its nutrient needs, the crop suffers. For example, a lack of nitrogen may lead to destruction of a crop's leaves. Additionally, once the nitrogen concentration in a plant decreases below a critical threshold, photosynthesis and dry matter accumulation is negatively impacted. An end result is that the yield of a crop which does not receive enough nutrients is decreased.

While nutrients in the soil are important to plant growth, it is difficult to determine when soil lacks one or more nutrients without performing nutrient tests. Additionally, the impact of a specific nutrient application is not readily apparent. For example, an application of forty pounds per acre of nitrogen at one time may result in a net increase of ten pounds of nitrogen per acre available to a crop due to nitrogen loss through a variety of factors and low transmission rates to the crop. The same application of forty pounds per acre of nitrogen at another time may result in the majority of the applied nitrogen being available to a crop. Without an understanding of all of the factors that affect whether a crop will receive the nitrogen added to a field, nitrogen application tends to be relatively blind. A farmer may apply nitrogen to a field at specific stages in a crop's development or when the crop appears to be suffering from a lack of nitrogen. Such applications of nitrogen are inefficient as they either involve wasting nitrogen or not adding enough nitrogen to satisfy the needs of a plant. Additionally, nitrogen lost to the field through leaching may create environmental problems when the nitrogen joins the watershed.

To identify nutrient content values in soil, a computer system may run a nutrient content model which takes in specific input values, such as temperature, soil type, crop type, and precipitation, and transforms the values to identify a nutrient content in the soil at various different points. While a nutrient content model is useful for generally identifying how much of a particular nutrient is in the soil, nutrient content models are not foolproof. Nutrient content models are subject to various sources of errors, such as errors in the input data, errors in universal parameters, and errors based on physical processes which are not being modeled.

A second method of identifying nutrient content values in soil is to measure the nutrient content in the soil using techniques such as near infrared reflectance spectroscopy on core samples removed from the field. Measurements of nutrient content in soil can be extremely accurate for the source of the soil sample. A problem with basing farming practices on measurements of nutrient practices is that a farmer would have to constantly be measuring the nutrient contents in a large number of locations.

Often, soil measurements are taken from a field at limited points in time. For example, farmers often take a measurement of nutrient content prior to side dressing in various locations across the field. Thus, as there are often limitations to the number of nutrient content measurement values received for a particular field, there is a need for a system which increases the accuracy in estimating nutrient content in soil using only a limited number of samples of nutrient content in the soil.

SUMMARY

The appended claims may serve as a summary of the disclosure.

BRIEF DESCRIPTION OF THE DRAWINGS

In the drawings:

FIG. 6 depicts an example embodiment of a spreadsheet view for data entry.

DETAILED DESCRIPTION

Figure 1:
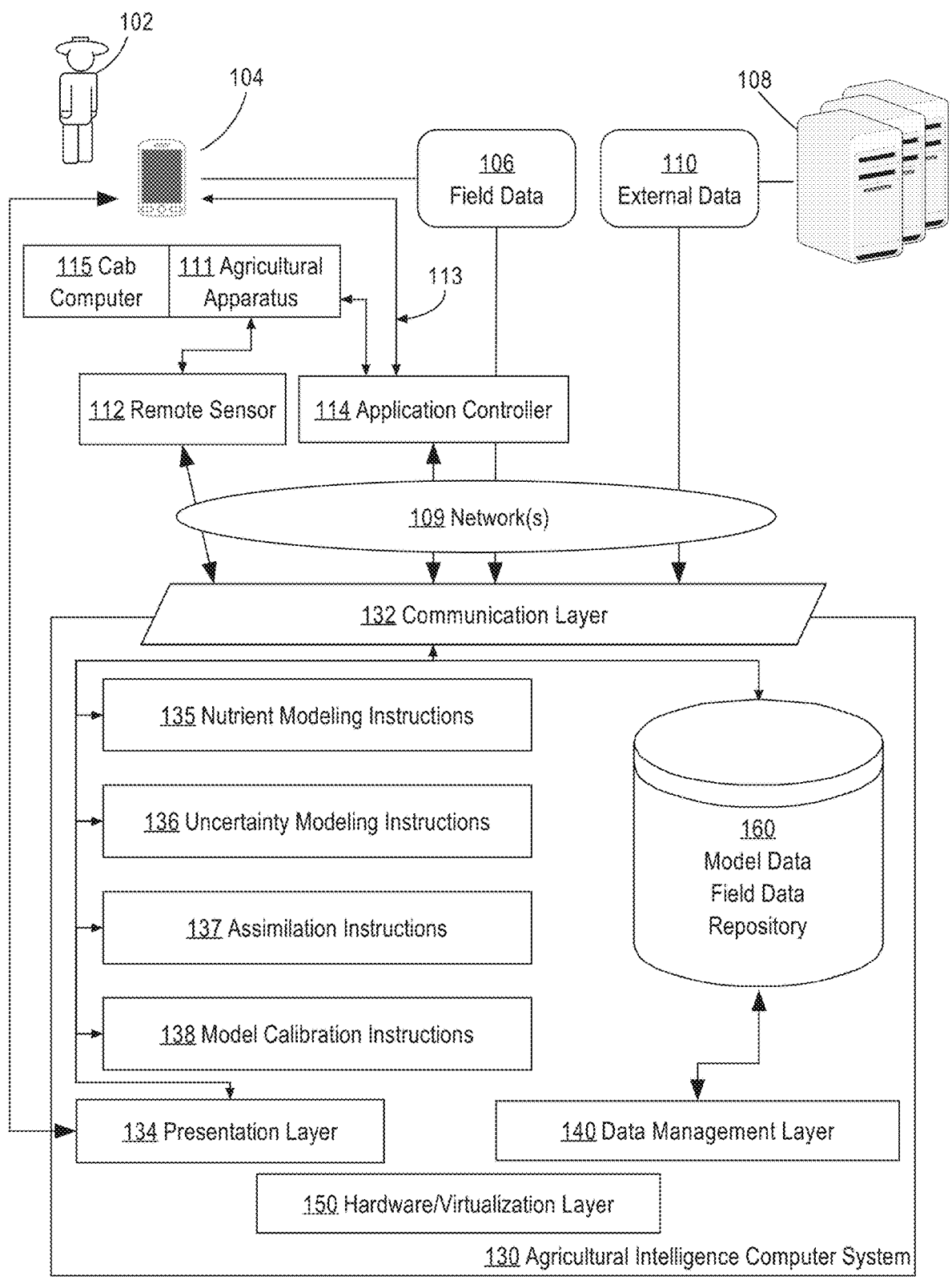
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:
 1. GENERAL OVERVIEW
 2. EXAMPLE AGRICULTURAL INTELLIGENCE COMPUTER SYSTEM
  2.1. STRUCTURAL OVERVIEW
  2.2. APPLICATION PROGRAM OVERVIEW
  2.3. DATA INGEST TO THE COMPUTER SYSTEM
  2.4. PROCESS OVERVIEW—AGRONOMIC MODEL TRAINING
  2.5. IMPLEMENTATION EXAMPLE—HARDWARE OVERVIEW
 3. NUTRIENT MEASUREMENT ASSIMILATION
  3.1. NUTRIENT CONTENT MODEL
  3.2. NUTRIENT CONTENT MEASUREMENTS
  3.3. UNCERTAINTY MODELING
  3.4. IDENTIFYING PARAMETERS TO PERTURB
  3.5. IDENTIFYING MEASUREMENT UNCERTAINTY
  3.6. ASSIMILATING DATA POINTS
  3.7. MODEL CALIBRATION
 4. DATA USAGE
  4.1. AGRONOMIC MODELS
  4.2. RECOMMENDATIONS
 5. BENEFITS OF CERTAIN EMBODIMENTS
 6. EXTENSIONS AND ALTERNATIVES

1. General Overview

Aspects of the disclosure generally relate to computer-implemented techniques for improving a nutrient content model using one or more soil samples at a particular field. In an embodiment, an agricultural intelligence computer system is programmed to compute a nutrient content value for a particular field using received input values and a nutrient content model. The agricultural intelligence computer also receives a soil sample measurement value for the particular field corresponding to the computed nutrient content value. The agricultural intelligence computer system computes an uncertainty in the nutrient content model and an uncertainty in the received soil sample measurement value. Based on the computed uncertainties, the computed nutrient content value, and the soil sample measurement value, the agricultural intelligence computer system computes an assimilated nutrient content value for the particular field.

In an embodiment, a method comprises storing, in digital memory of a computer system, a digital model of nutrient content in soil of one or more fields over a particular period of time, wherein the digital model comprises a plurality of values and expressions that are stored in the digital memory and define transformations of or relationships between the values and produce estimates of nutrient content values describing amounts of various chemicals in the soil; receiving, at the computer system over one or more networks from a client computing device, one or more digital measurement values specifying measurements of nutrient content in soil at a particular field of the one or more fields at a particular time within the particular period of time; identifying a modeled nutrient content value representing an estimate of nutrient content in the soil at the particular field at the particular time; identifying a modeling uncertainty value for the digital model of nutrient content wherein the modeling uncertainty value represents a magnitude of error in the digital model; identifying one or more measurement uncertainty values for each of the one or more digital measurement values specifying measurements of nutrient content respectively wherein each of the modeling uncertainty values represents a magnitude of error in a corresponding digital measurement value; generating and displaying, based, at least in part, on the modeling uncertainty value and one or more measurement uncertainty values, an assimilated nutrient content value representing an improved estimate of nutrient content in the soil at the particular field at the particular time.

2. Example Agricultural Intelligence Computer System

2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) pesticide data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines or harvesters. Application controller 114 is communicatively coupled to agricultural intelligence computer system 130 via the network(s) 109 and is programmed or configured to receive one or more scripts to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGR-ESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
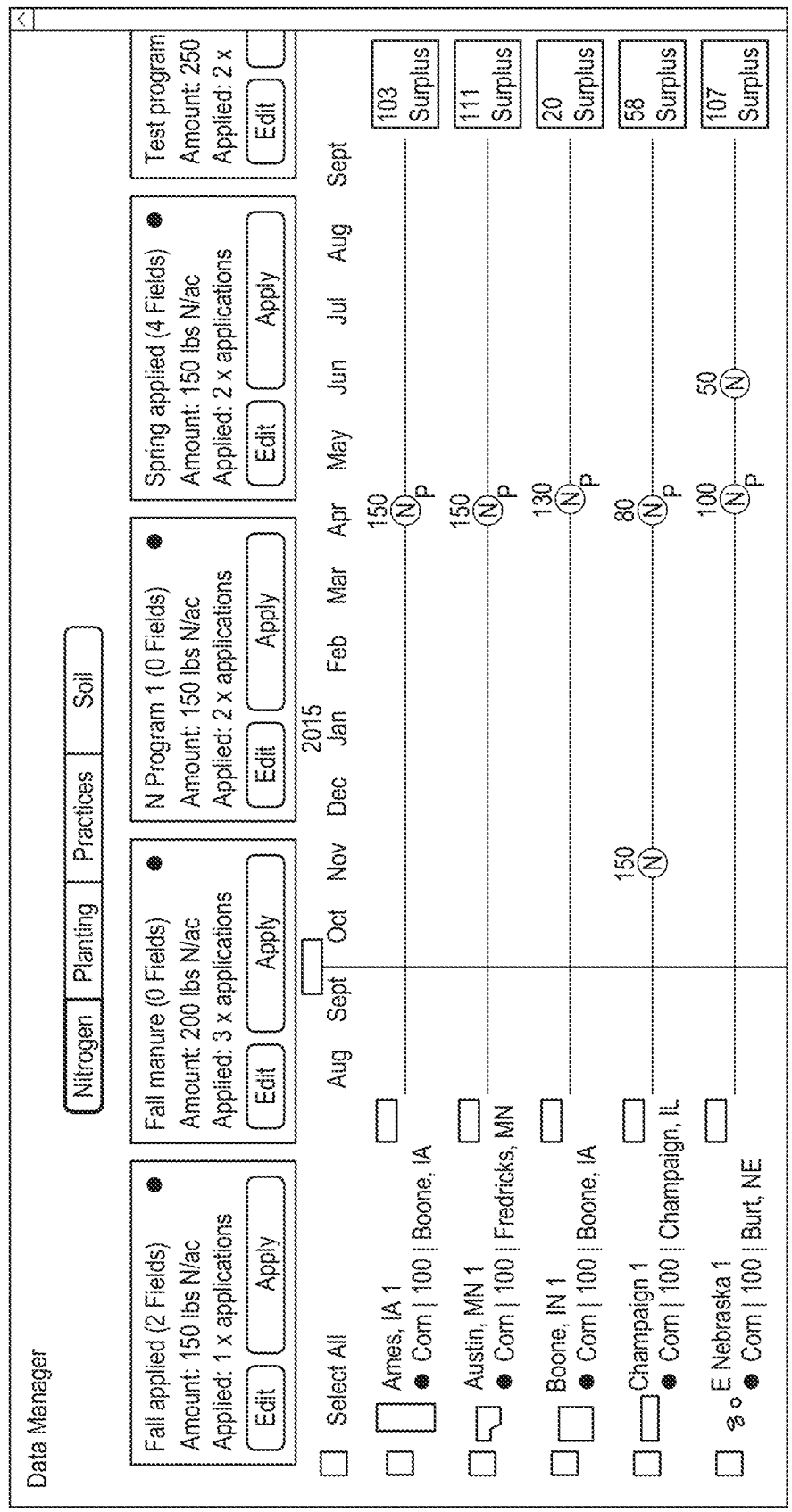
FIG. 5 depicts an example embodiment of a timeline view for data entry.

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Fall applied" program selected, which includes an application of 150 lbs N/ac in early April. The data manager may provide an interface for editing a program. In an embodiment, when a particular program is edited, each field that has selected the particular program is edited. For example, in FIG. 5, if the "Fall applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Fall applied" program is no longer being applied to the top field. While the nitrogen application in early April may remain, updates to the "Fall applied" program would not alter the April application of nitrogen.

Figure 6:
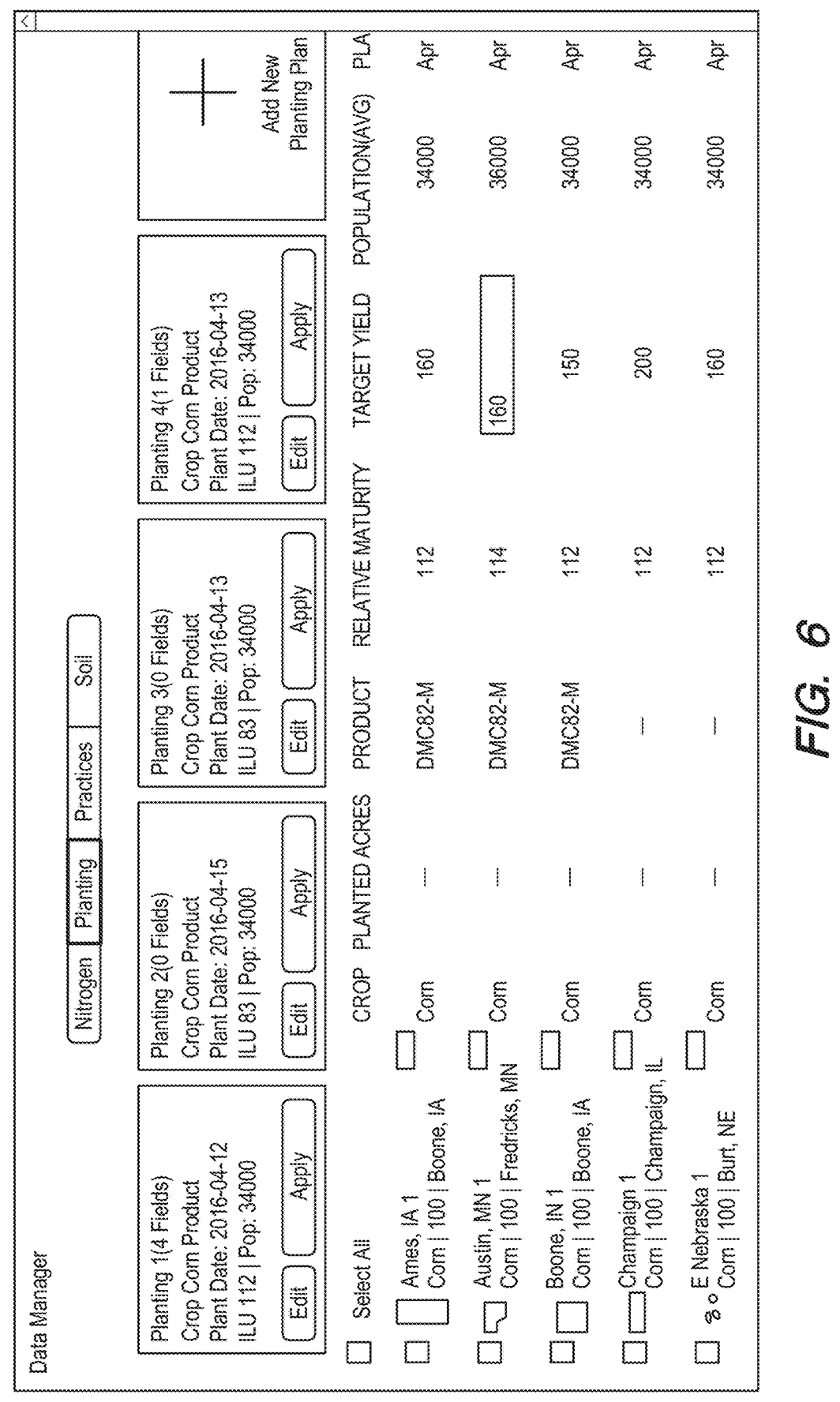

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In one embodiment, each of nutrient modeling instructions 135, uncertainty modeling instructions 136, assimilation instructions 137, and model calibration instructions 138 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the nutrient modeling instructions 135 may comprise a set of pages in RAM that contain instructions which when executed cause performing the nutrient modeling functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of the nutrient modeling instructions 135, uncertainty modeling instructions 136, assimilation instructions 137, and model calibration instructions 138 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Nutrient modeling instructions 135 comprise computer readable instructions which, when executed by one or more processors, causes agricultural intelligence computer system 130 to perform computation of nutrient values in soil using soil data, crop data, and weather data. Uncertainty modeling instructions 136 comprise computer readable instructions which, when executed by one or more processors, causes agricultural intelligence computer system 130 to perform estimation of uncertainty values corresponding to measurement values of nutrient content and modeled values of nutrient content. Assimilation instructions 137 comprise computer readable instructions which, when executed by one or more processors, causes agricultural intelligence computer system 130 to perform computation of nutrient values in soil based on prior computations of nutrient values in soil and measured values of nutrient content in soil.

Model calibration instructions 138 comprise computer readable instructions which, when executed by one or more processors, causes agricultural intelligence computer system 130 to perform calibration of nutrient modeling instructions 135 based, at least in part, on computed nutrient values.

Figure 4:
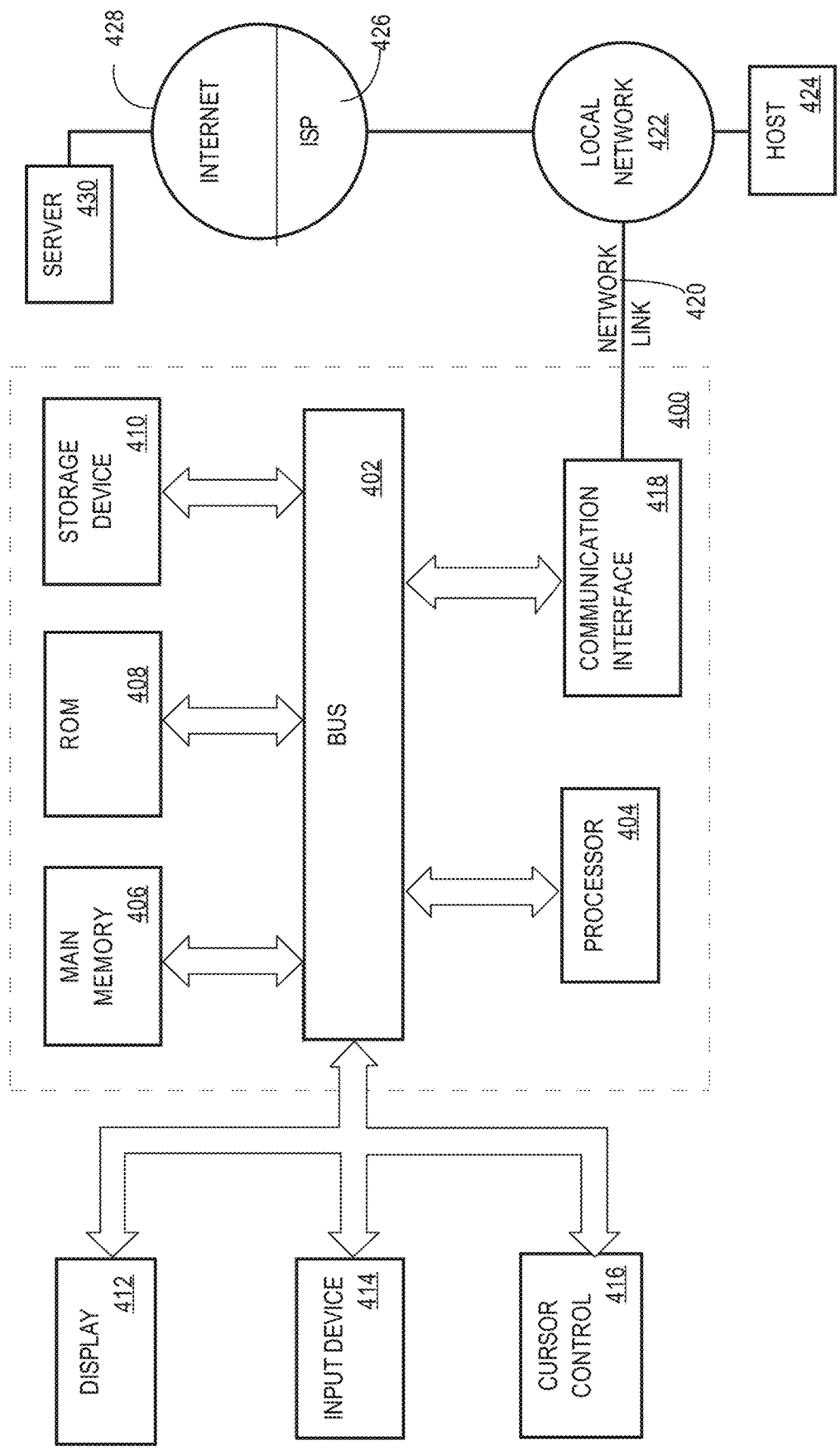
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

Figure 2:
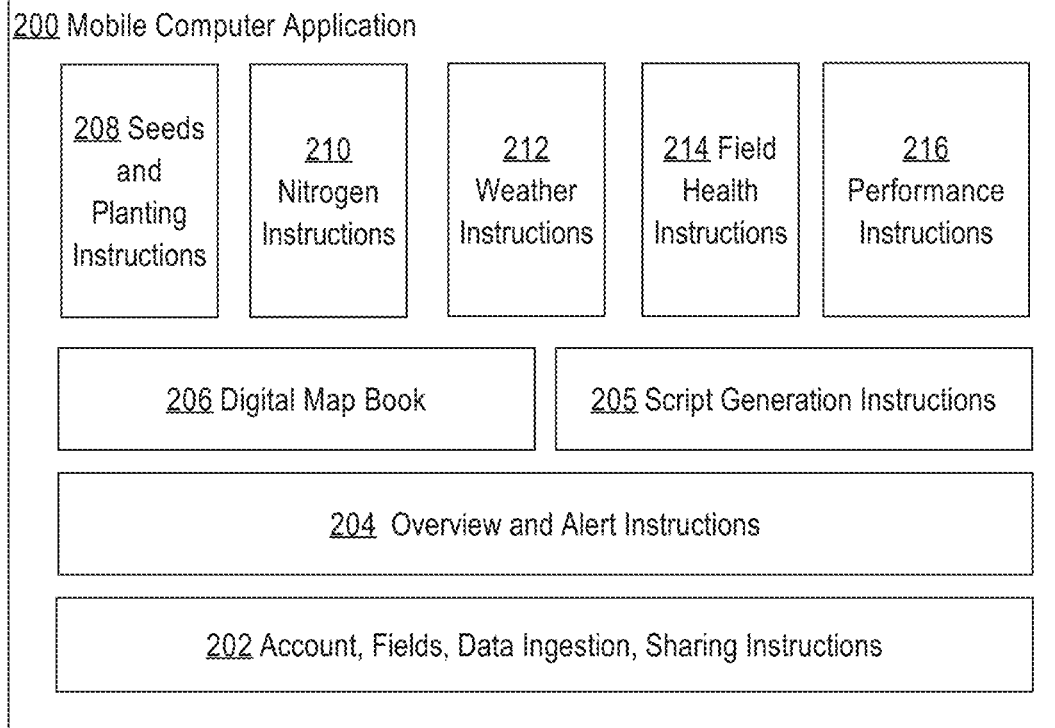
FIG. 2 illustrates two views of an example logical organization of sets of instructions in main memory when an example mobile application is loaded for execution.
Figure 2:
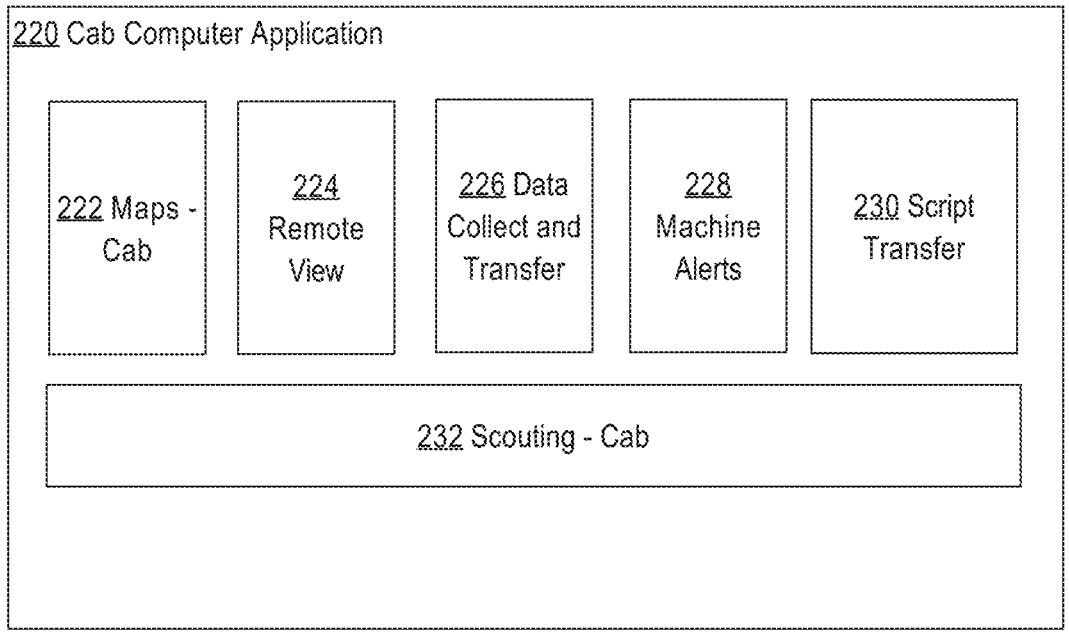

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account-fields-data ingestion-sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of application zones and/or images generated from subfield soil data, such as data obtained from sensors, at a high spatial resolution (as fine as 10 meters or smaller because of their proximity to the soil); upload of existing grower-defined zones; providing an application graph and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields that have been defined in the system; example data may include nitrogen application data that is the same for many fields of the same grower, but such mass data entry applies to the entry of any type of field data into the mobile computer application 200. For example, nitrogen instructions 210 may be programmed to accept definitions of nitrogen planting and practices programs and to accept user input specifying to apply those programs across multiple fields. "Nitrogen planting programs," in this context, refers to a stored, named set of data that associates: a name, color code or other identifier, one or more dates of application, types of material or product for each of the dates and amounts, method of application or incorporation such as injected or knifed in, and/or amounts or rates of application for each of the dates, crop or hybrid that is the subject of the application, among others. "Nitrogen practices programs," in this context, refers to a stored, named set of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium) application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, hybrid, population, SSURGO, soil tests, or elevation, among others. Programmed reports and analysis may include yield variability analysis, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 230 may be programmed to display location-based alerts and information received from the system 130 based on the location of the agricultural apparatus 111 or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. Nos. 8,738,243 and 9,999,175, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus. Such controllers may include guidance or motor control apparatus, control surface controllers, camera controllers, or controllers programmed to turn on, operate, obtain data from, manage and configure any of the foregoing sensors. Examples are disclosed in U.S. Pat. No. 9,922,405 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4 Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
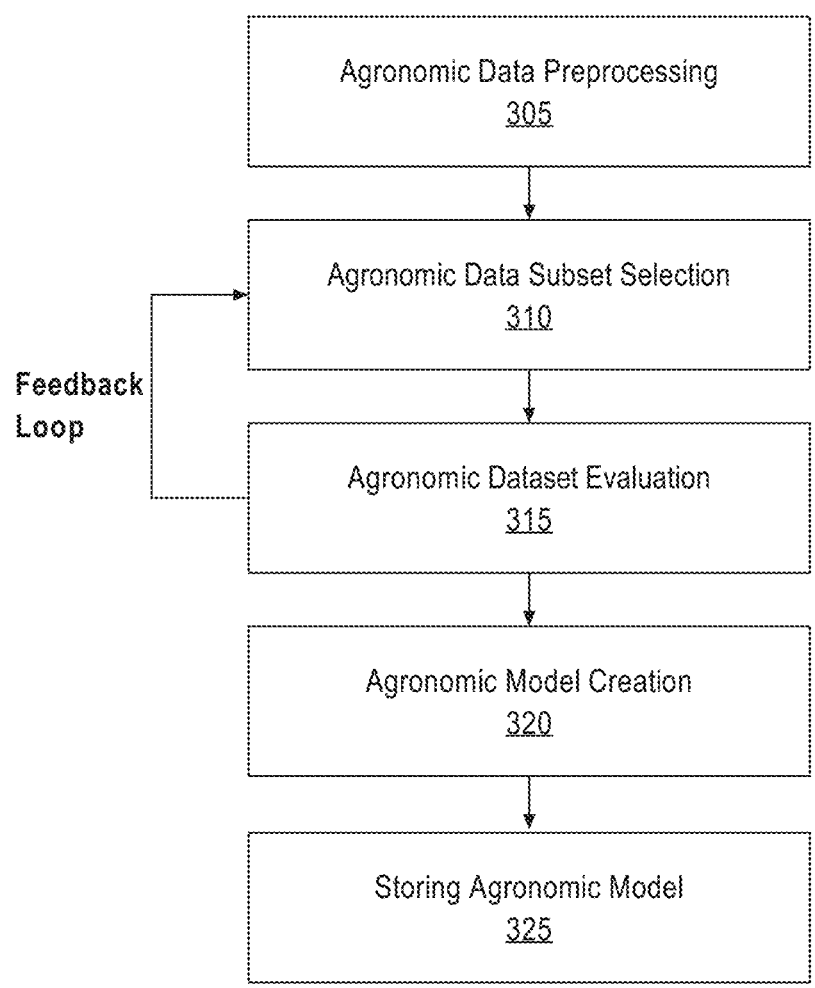
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise and distorting effects within the agronomic data including measured outliers that would bias received field data values. Embodiments of agronomic data preprocessing may include, but are not limited to, removing data values commonly associated with outlier data values, specific measured data points that are known to unnecessarily skew other data values, data smoothing techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared using cross validation techniques including, but not limited to, root mean square error of leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5 Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Nutrient Measurement Assimilation

Figure 7:
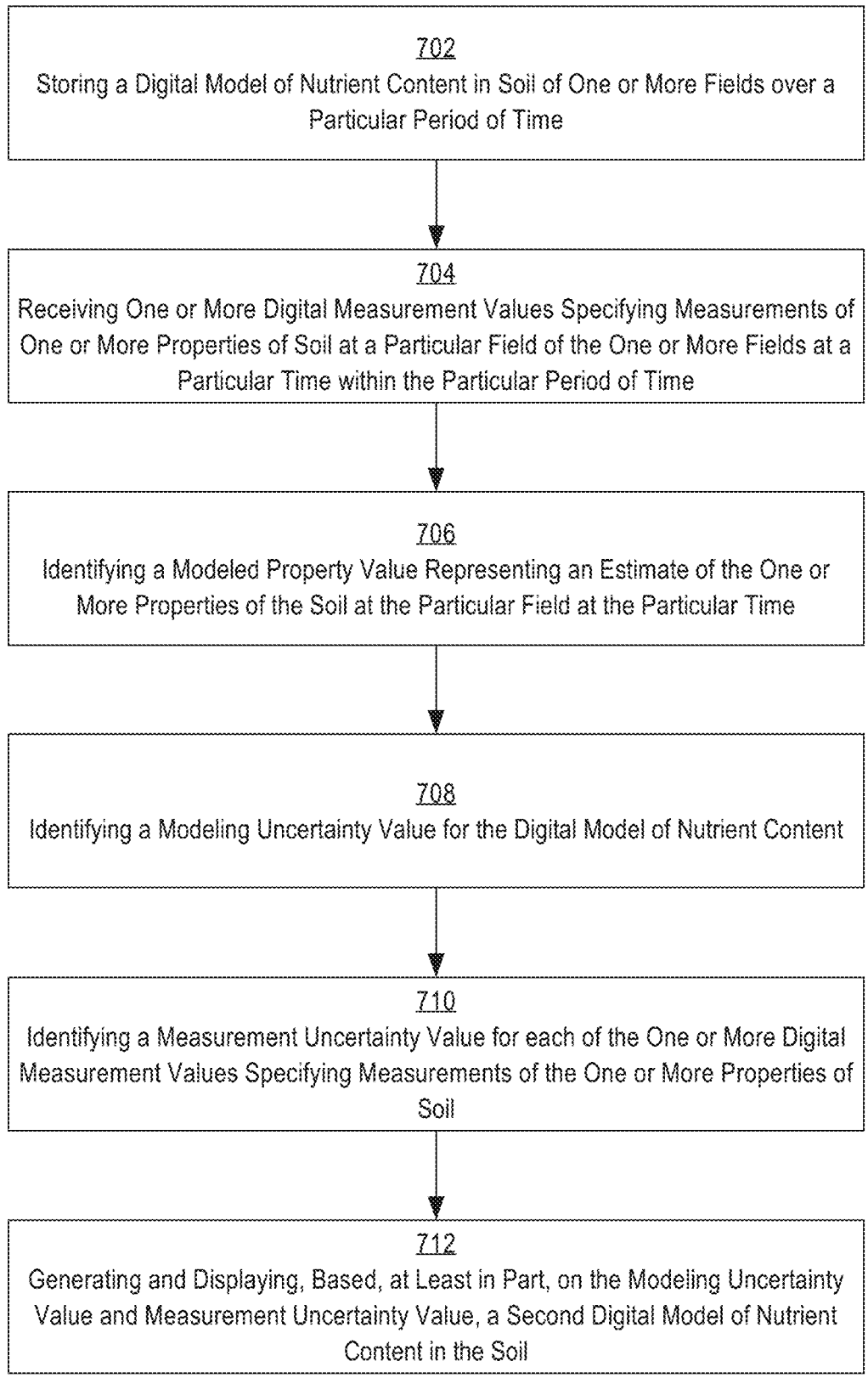
FIG. 7 depicts an example method for assimilating a single data point into a model of nutrient content in soil.

FIG. 7 depicts an example method for assimilating a single data point into a model of nutrient content in soil.

3.1 Nutrient Content Model

At step 702, a digital model of nutrient content in soil of one or more fields over a particular period of time is stored. A digital model of nutrient content in soil generally comprises a plurality of values defining amounts of nutrient in soil at a particular field over a particular period of time. For example, a digital model of nitrogen content in soil may identify a number of pounds per acre of nitrogen in a particular field or particular section of a field at various points in time during the development of a crop on the field. The various points in time may include daily estimates of nutrient content or estimates related to a life cycle of a crop. For example, a digital model of nutrient content in soil may identify nutrient concentrations at various vegetative growth stages, such as the growth emergence stage, the fully visible tassel stage, and/or any intermediate stages, and at various reproductive stages. The digital model of nutrient content may also comprise a plurality of values defining other characteristics of the soil at the particular field over the particular period of time such as moisture content and temperature of the soil.

The digital model of nutrient content in soil may identify one or more properties of the soil, such as nutrient content, temperature, and moisture content, based on one or more data inputs, one or more parameters, and one or more structural relationships. Data inputs refer to data values specific to a field. Examples of data inputs include soil pH, percentage of organic matter in soil, percentage of sand, silt, and clay in soil, percentage of various nutrients in soil, type and amount of fertilizer added to a particular field, tilling types, farming practices, irrigation, temperature, precipitation, and crop type. Parameters are values that parametrize a family of models and often cannot be directly measured. Examples of parameters include nitrification rate, rate of soluble organic nitrogen breakdown, rainfall bypass through residue, coefficient of leaching for nitrate, ammonium, and urea, denitrification rate, hydrolysis rate of urea, clay ammonium absorption factor, and Darcian nitrogen diffusion factor. Parameters may vary from field to field. For example, nitrification and leaching rates may be affected by temperature and type of soil. Structural relationships refer to estimated or known relationships between various factors. Examples of structural relationships include computation instructions for estimating leaching based on soil type, estimating denitrification rate based on soil moisture, and for defining other physical relationships.

Agricultural intelligence computer system 130 may store a digital model of nutrient content for a particular field for a particular period of time. For example, agricultural intelligence computer system 130 may receive a request from field manager computing device 104 to model nutrient values in a field associated with field manager computing device 104 during the development of a particular crop on the field. Agricultural intelligence computer system 130 may also receive field data 106 from field manager computing device 104 and/or external data 110 from external data server computer 108. Field data 106 may include information relating to the field itself, such as field names and identifiers, soil types or classifications, tilling status, irrigation status, soil composition, nutrient application data, farming practices, and irrigation data. As used herein, a 'field' refers to a geographically bounded area comprising a top field which may also comprise one or more subfields. Field data 106 may also include information relating to one or more current crops, such as planting data, seed type or types, relative maturity levels of planted seed or seeds, and seed population. Additionally, field data 106 may include information relating to historical harvest data including crop type or classification, harvest date, actual production history, yield, grain moisture, tillage practices, and manure application history.

External data 110 may include any additional data about the field, the one or more crops, weather, precipitation, meteorology, and/or soil and crop phenology. Weather, precipitation, and meteorology may be received as current temperature/precipitation data and future forecast data for the one or more fields. Current temperature/precipitation data may include measurements of temperature. Additionally, and/or alternatively, the current temperature/precipitation data and forecast data may include data at specific observation posts that is interpolated to locations in between the observation posts, such as in Non-Provisional application Ser. No. 14/640,900 the entire contents of which are incorporated by reference as if fully set forth herein. External data 110 may also include soil data for the one or more fields. For example, the Soil Survey Geographic database (SSURGO) contains per layer soil data at the sub field level for areas in the United States, including percentage of sand, silt, and clay for each layer of soil. In an embodiment, external data 110 includes data received from SSURGO or other sources of soil data. In an embodiment, external data is supplemented with grower data and/or laboratory data. For example, soil taken from the one or more fields may be used to adjust the external data received from SSURGO where the external data is inaccurate.

Agricultural intelligence computer system 130 may use field data 106 and external data 110 to create a digital model of nutrient content in soil at the particular location. For example, agricultural intelligence computer system 130 may store initial inputs for the particular field. Agricultural intelligence computer system 130 may also estimate parameters for the particular field and store the parameters for the particular field. Agricultural intelligence computer system 130 may additionally compute parameters based on received external data 110. For example, if a particular parameter is based on temperature, agricultural intelligence computer system 130 may use temperature forecast data and/or temperature measurements to compute the particular parameter.

3.2 Nutrient Content Measurements

At step 704, one or more measurement values specifying measurements of one or more properties of soil at a particular field of the one or more fields at a particular time within the period of time is received. For example, measurements of soil nutrient values, soil moisture values, and/or temperature may be taken before planting, before side dressing, and before harvest of a crop. Agricultural intelligence computer system 130 may receive measurement data from field manager computing device 104 identifying one or more measurements of the one or more properties within the soil at one or more locations across the field. The measurements of the one or more properties may correspond to core samples taken at various locations across the field. The results of measurements may be sent to agricultural intelligence computer system 130 through a graphical user interface executing on field manager computing device 104.

The particular time may correspond to a specific growth stage of the crop development. For example, soil samples tend to be taken at the V6-V8 stages of crop development. The soil samples may include per layer analysis of nutrient values. For example, a first measurement of NO may correspond to soil at 0-30 cm from the surface at a particular location while a second measurement of NO may correspond to soil at 30-60 cm from the surface at the particular location. Agricultural intelligence computer system 130 may receive data identifying the particular time along with the measurement of nutrient content. For example, agricultural intelligence computer system 130 may cause displaying a graphical user interface on a client computing device with options to identify a nutrient content of soil, a temperature of soil, and/or a moisture content of soil, a location of the measurement, and a date and time of measurement.

3.3 Uncertainty Modeling

At step 706, a modeled soil property value representing an estimate of the one or more properties of the soil at the particular field at the particular time is identified. For example, agricultural intelligence computer 130 may use the digital model of nutrient content in soil of the one or more fields over the particular period of time to estimate the nutrient content at a specific time in various physical locations of the particular field. Nutrient content estimates may include estimates of potassium, phosphorus, and nitrogen levels in the soil at the various physical locations. In an embodiment, the particular time corresponds to a time in which a measurement of nutrient content was taken. For example, agricultural intelligence computer system 130 may receive soil measurement values from a field manager computing device with an indication of a location of the soil measurement and a date and/or time of the soil measurement. In response, agricultural intelligence computer system 130 may compute the nutrient contents in soil for the indicated location and the indicated date and/or time.

At step 708, a modeling uncertainty value for the digital model of nutrient content is identified. For example, agricultural intelligence computer system 130 may identify an uncertainty in the estimates of nutrient content, soil moisture, and/or soil temperature based on the digital model of nutrient content. The modeling uncertainty may comprise three types of uncertainty: input uncertainty, parameter uncertainty, and structural uncertainty. The different types of uncertainty may be computed as a total uncertainty for the model. Additionally, and/or alternatively, the different types of uncertainty may be computed separately to identify three different uncertainties in the estimate of a particular soil property at the particular time. The three uncertainties may then be combined to identify an overall uncertainty for the modeled soil property value. While generally three sources of uncertainty exist in the model of nutrient content, in an embodiment, less than all of the types of uncertainty are identified in step 708. For example, structural uncertainty may be ignored due to difficulties in determining the uncertainties that exist due to physical interactions which are not being modeled. Agricultural intelligence computer system 130 may identify the uncertainty in the modeled value of nutrient content based on uncertainty in various parameters and inputs without taking into account the structural uncertainty.

Structural uncertainty generally refers to uncertainty in the model of nutrient content that is created by a failure to account for particular physical reactions. For example, a large number of different elements, from temperature to moisture content, can have an impact on the nutrient content in the soil. Regardless of how complete the model of nutrient content is, there may be one or more physical interactions that affect the nutrient content in the soil which are not being accounted for in the model. Additionally, effects of temperature, soil moisture, nutrient content, and other physical properties from surrounding locations may be computationally expensive to model. These physical interactions may cause the modeled nutrient value to differ from the actual nutrient value. One method of estimating the errors based on structural uncertainty is to run the model against a plurality of measurements in a single location or a plurality of locations. Based on differences between the modeled values and the measured values, agricultural intelligence computer system 130 may identify a structural uncertainty to the model. Structural uncertainty may also be estimated based on different nutrient models computing nutrient values for a particular location. This structural uncertainty may be computed for specific locations and/or times of the year. For example, if the model of nutrient content tends to be less accurate at high temperatures, locations which experience high temperatures may be associated with a higher structural uncertainty than location which experience low temperatures.

Input uncertainty generally refers to uncertainty in one or more received values which are used to generate the model. For example, input uncertainty may refer to uncertainty in the initial soil nutrient measurements for the field. Additionally, and/or alternatively, input uncertainty may refer to an uncertainty in temperature and/or precipitation predictions/measurements. For example, various modeling techniques may be used to create probabilistic estimates of precipitation and/or temperature at particular locations and times based on prior precipitation and temperature measurements. Various modeling techniques may also be used to identify uncertainties in temperature and precipitation measurements at particular locations. For example, radar based precipitation measurements at particular locations include uncertainty due to various drop sizes and rainfall density leading to similar reflectivity measurements. A quantification of the uncertainty in the radar based precipitation measurements may be identified as uncertainty in the particular inputs.

Parameter uncertainty generally refers to uncertainty in one or more computed or estimated values which are not measured directly. For example, the rate at which organic matter converts into ammonium may be estimated based on a plurality of field trials and/or experiments. The rate of conversion of organic matter may be computed from measurements at various temperatures, moisture levels, and soil nutrient levels in order to identify a dependence of the rate of conversion on various factors. Even with substantial experimentation and field trials, an uncertainty in the rate of conversion of organic matter will exist due to unidentified factors which affect the rate of conversion of organic matter. The uncertainty may be quantified through field trials and/or experiments and stored with the nutrient content model. Where uncertainties are identified as dependent on one or more other inputs or parameters, the inputs and parameters which affect the uncertainty values may be stored along with the different uncertainties and identification of the affected parameter.

The uncertainties in parameters and inputs may be used to identify an uncertainty in the model of nutrient content. One method of identifying an uncertainty in the overall model of nutrient content based on a plurality of uncertainties in parameters and inputs is to identify values of each parameter and input which lead to a minimum nutrient content value and values of each parameter and input which lead to a maximum nutrient content. Based on the minimum parameters/inputs and the maximum parameters/inputs, agricultural intelligence computer system 130 may compute a minimum nutrient content value and a maximum nutrient content value. The minimum and maximum values may be used to identify a range of nutrient content in the field at the particular time.

In an embodiment, agricultural intelligence computer system 130 takes into account effects of inputs and parameters on other inputs and parameters in computing uncertainty in the model of nutrient content. For example, interactions between particular parameters and inputs may result in one input value resulting in a minimum nutrient content for one set of inputs and parameters but not resulting in a minimum nutrient content for a second set of inputs and parameters. Additionally, for a particular input type, such as temperature, different input values may affect the value of a particular parameter and/or the uncertainty for a particular parameter. Thus, while changing the input on its own may lead to a particular nutrient content value, altering the parameters affected by the input as well may lead to a different nutrient content value.

Figure 8:
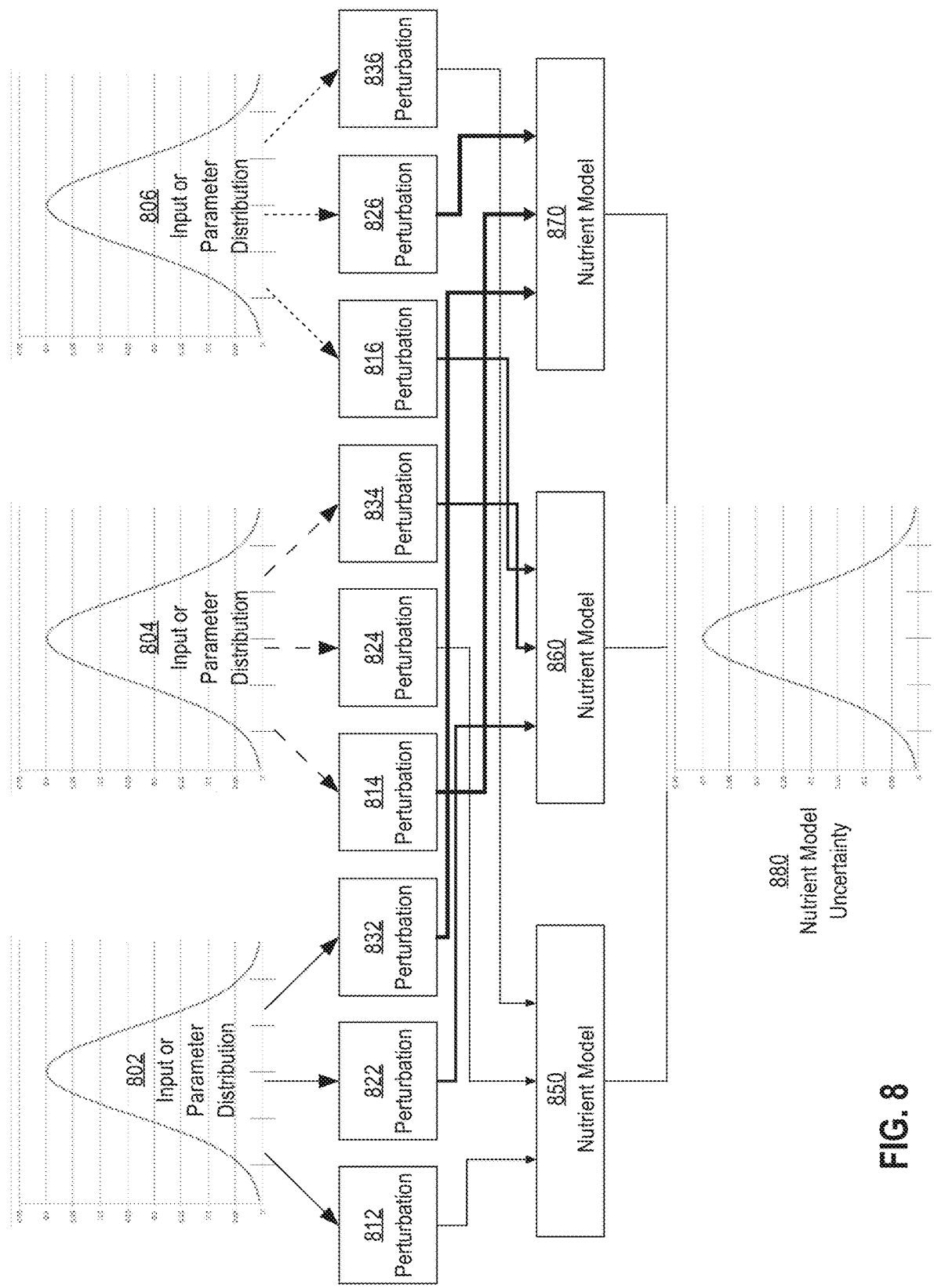
FIG. 8 depicts an example method for identifying uncertainty in the nutrient content model by perturbing different parameters.

In an embodiment, agricultural intelligence computer system 130 estimates uncertainty in the nutrient content model by combining different perturbations of various inputs and parameters to compute different level of nutrient content in the soil. FIG. 8 depicts an example method for identifying uncertainty in the nutrient content model by perturbing different parameters. FIG. 8 includes input or parameter distribution 802, input or parameter distribution 804, and input or parameter distribution 806. Each of distributions 802, 804, and 806 correspond to particular input or parameter values and an uncertainty in each of the input or parameter values. For example, distribution 802 may refer to precipitation on a particular day which is estimated at 2.1" with an uncertainty of 0.2". Distributions 804 and 806 may refer to other parameters or inputs with different uncertainties. For example, distribution 804 may refer to an estimate and uncertainty in the rate of conversion from organic matter to ammonium. While FIG. 8 depicts three distributions, in an embodiment an estimate and uncertainty for each input and parameter with a known or estimated uncertainty is used. Additionally, and/or alternatively, uncertainties of specific parameters and inputs which cause larger changes to the nutrient content model are utilized while parameters and inputs which do not have a significant effect on the model are not used.

In an embodiment, each utilized input and parameter is perturbed to generate a plurality of perturbations for each input and parameter. In an embodiment, perturbing a parameter or input comprises generating a particular number of spaced values for the parameter or input between a lower bound for the parameter and the upper bound of the parameter. The values may be evenly spaced and/or spread out based on prior sensitivity analyses. For example, in the precipitation example above, one hundred evenly spaced values may be generated between 1.9" and 2.3". Thus, the perturbations for the precipitation example may include values of 1.9", 1.904", and 1.908". In some embodiments, perturbing the parameter or input comprises generating a particular number of evenly spaced values for the parameter or input between a lower bound and the default value and generating a particular number of evenly spaced values for the parameter or input between the default value and the upper bound. By generating an equal number of values between the lower bound and the default value and between the default value and the upper bound, agricultural intelligence computer system 130 can account for uneven distributions in the uncertainty of a particular parameter or input. For example, if the estimated precipitation on a particular day is 2.1" but the range of precipitation values is 1.8" to 2.2", the number of values generated between 1.8" and 2.1" would equal the number of values between 2.1" and 2.2".

In an embodiment, perturbing the inputs and/or parameters comprises sampling from distributions associated with each of the inputs and/or parameters. For example, a Gaussian distribution for a particular parameter and/or input may be identified by a mean value for the parameter and/or input and a standard deviation for the parameter and/or input. Agricultural intelligence computer system 130 may execute sampling instructions to sample a particular number of non-repeating values from the distribution. By sampling from a distribution of values for the input and/or parameter, agricultural intelligence computer system 130 preserves the shape of the distribution, thereby propagating the error of the input and parameters to the uncertainty for the digital model of nutrient content.

In an embodiment, an equal number of perturbations are generated for each parameter or input. For example, in FIG. 8, perturbations 812, 822, and 832 are generated from input or parameter distribution 802, perturbations 814, 824, and 834 are generated from input or parameter distribution 804, and perturbations 816, 826, and 836 are generated from input or parameter distribution 806. While FIG. 8 depicts three inputs and/or parameters and three perturbations per input and/or parameter, an embodiment may include any number of inputs and/or parameters and hundreds of perturbations for each input and/or parameter. Additionally, agricultural intelligence computer system 130 may generate multiple sets of perturbations for each input or parameter. For example, while each set of perturbations for a particular input may comprise one hundred values, agricultural intelligence computer system 130 may generate thirty sets of values for the particular input, thereby generating three thousand perturbations of the particular parameter.

In an embodiment, agricultural intelligence computer system 130 randomly selects perturbations from each input or parameter and uses the randomly selected perturbation values to run the model of nutrient content. For example, nutrient model 850 is run with perturbation 812, perturbation 824, and perturbation 836. In an embodiment, the randomly selected nutrient values are taken from a single set of values for each input or parameter without replacement. For example, if thirty sets of one hundred perturbations are created for each input or parameter, agricultural intelligence computer system 130 may randomly select from the first set of one hundred perturbations for each input or parameter without replacement until every value of the one hundred values has been used. Agricultural intelligence computer system 130 may then randomly select from the second set of one hundred perturbations for each input or parameter without replacement until every value of the second one hundred values has been used. In an embodiment, agricultural intelligence computer system 130 only selects combinations of perturbations that have not already been utilized. For example, if in a tenth set of one hundred perturbations agricultural intelligence computer system 130 selects a combination of inputs and parameters that are the same as a selection from a prior set of one hundred perturbations, agricultural intelligence computer system 130 may reselect one or all of the perturbations.

In an embodiment, agricultural intelligence computer system 130 first computes perturbations in independent values before computing perturbations in dependent values. Independent values, as used herein, refer to the values of inputs or parameters which are independent of the values of other inputs or parameters. For example, the temperature in a particular location may be directly measured and therefore may be unaffected by changes in other inputs while soil moisture may change depending on temperature, precipitation, and soil nutrient content values. As another example, certain parameters may be considered global parameters in that they do not vary from field to field while other parameters may be dependent on soil moisture or temperature. Agricultural intelligence computer system 130 may initially perturb independent inputs and parameters to generate a particular combination of perturbations. Based on the combination of perturbations, agricultural intelligence computer system 130 may compute additional parameter or inputs and then perturb the values of the additional parameter or inputs.

In an embodiment, agricultural intelligence computer system 130 identifies combinations of perturbations that do not yield sensible outputs and result in a failed model run. For example, some parameters may be related to others such that a high perturbation of one parameter should result in a high perturbation in a second parameter. This may occur if the variability of the parameters have the same source and/or if the variability of a first parameter is dependent on the variability of a second parameter. If one or more of the selected parameters or values is inconsistent with one or more other parameters or values, agricultural intelligence computer system 130 may discard the results of running the nutrient content model for that set of parameters and/or values. Additionally, and/or alternatively, if the results of running the nutrient content model are not physically sensible outputs, agricultural intelligence computer system 130 may determine that the particular set of parameters and/or inputs has resulted in a failed model run and discard the results. For example, if agricultural intelligence computer system 130 models a top and a bottom layer of soil as having a high moisture content, but a middle layer of soil as having a negligible moisture content, agricultural intelligence computer system 130 may determine that the results of the nutrient content model are not sensible and may thus be discarded.

In an embodiment, agricultural intelligence computer system 130 generates a nutrient model uncertainty from the viable results of each model of nutrient content. For example, nutrient model 850, nutrient model 860, and nutrient model 870 may each produce different results for nutrient content measurements based on the perturbations of parameters and/or inputs. The results for nutrient content may include results for various types of nutrients at various locations and soil levels. A nutrient uncertainty model may be generated for the results of each nutrient model at a particular soil level, location, nutrient type, and time. Thus, nutrient uncertainty model 880 may describe the uncertainty in a particular nutrient type at a particular location and soil level. The same perturbations of parameters and/or inputs may be used to generate uncertainty models for other locations. Additionally, and/or alternatively, the method of perturbing the parameters and/or inputs may be run independently for each location, each soil layer, and/or each nutrient type. Thus, different combinations of perturbations may be used for various locations across a field, various soil layers, and/or various nutrient types. In this manner, the modeling uncertainty can be localized to a particular location, soil level, and/or nutrient type.

In an embodiment, nutrient model uncertainty values are identified for a plurality of locations across a field. For example, inputs may be received at particular locations of a field. A modeling uncertainty may be identified for each of the particular locations of the field. Agricultural intelligence computer device 130 may utilize one or more modeling techniques to estimate uncertainties in the nutrient content model and/or in one or more parameters and/or inputs in different locations of the field at a particular time using the uncertainties at the particular locations. For example, agricultural intelligence computer system 130 may assume that the uncertainty values at each location is the product of a smooth underlying uncertainty curve across the one or more fields. Agricultural intelligence computer system 130 may determine the shape of the underlying curve using statistical modeling techniques, such as kriging, and sample from the underlying curve at each different location to obtain an uncertainty value for the location. Agricultural intelligence computer system 130 may utilize similar techniques to model uncertainty values across a parameter space. For example, agricultural intelligence computer system 130 may assume that uncertainty values at each parameter is the product of a smooth underlying curve across the parameter space and sample each uncertainty value across parameters.

3.4 Identifying Parameters to Perturb

In an embodiment, agricultural intelligence computer system 130 identifies sensitive parameters to perturb in order to decrease the computing power used in identifying the modeling uncertainty for a particular location. Computing a modeled nutrient content using uncertainties in each input and parameter may be costly given a complex model of nutrient content. Thus, in order to decrease the computing power used to identify the modeling uncertainty, agricultural intelligence computer system 130 may identify a subset of parameters and uncertainties which have the greatest effect on the nutrient content model when perturbed.

In an embodiment, agricultural intelligence computer system 130 identifies sensitive parameters and/or inputs by computing nutrient content values with perturbations of a single parameter and/or input. For example, agricultural intelligence computer system 130 may select a particular parameter and/or input to perturb for a plurality of nutrient content measurements while keeping the remaining parameters and/or inputs constant. Agricultural intelligence computer system 130 may run the model with the plurality of perturbations of the selected parameter and/or input for each of a plurality of years, locations, and/or management practices. Based on the nutrient contents for each of the perturbations, agricultural intelligence computer system 130 may identify a range and/or uncertainty in the model given perturbations of the selected parameter and/or input. By identifying modeling uncertainties for a selected parameter and/or input across time, space, and management practices, agricultural intelligence computer system 130 is able to determine an uncertainty that is not constrained by location, year, or management practice.

Agricultural intelligence computer system 130 may compute nutrient model uncertainties for each parameter and/or input while keeping the rest constant. Agricultural intelligence computer system 130 may then select the parameters and/or inputs which, when perturbed, create the greatest change in the model. The selected parameters and/or inputs may be used to compute the modeling uncertainty at a particular location and time. In an embodiment, agricultural intelligence computer system 130 may use data specific to a particular location, year, and/or management practice to identify sensitive parameters and/or inputs based on the location, year, and/or management practice. For example, agricultural intelligence computer system 130 may identify sensitive parameters and/or inputs for an initial application of 501*bs* of nitrogen across a plurality of locations and years and for an initial application of 1001*bs* of nitrogen across a plurality of locations and years. If the selected parameters and/or inputs differ between the 501*b* application and 1001*b* application trials, then when agricultural intelligence computer system 130 identifies the modeling uncertainty for a particular field, agricultural intelligence computer system 130 may select one or more parameters and/or inputs based on the nutrient application to the particular field.

3.5 Identifying Measurement Uncertainty

At step 710, a measurement uncertainty value for each of the one or more digital measurement values specifying measurements of the one or more properties of the soil is identified.

Identifying a measurement uncertainty value for a particular location and time may comprise identifying a variability within the field at a particular time. For example, agricultural intelligence computer system 130 may receive a plurality of measurements at different points of a field. Agricultural intelligence computer system 130 may identify measurements that relate to a particular region of the field that has undergone uniform management practices. For example, measurements from a portion of the field which received an initial application of 50 lbs of nitrogen may not be grouped with measurements from a portion of the field which received an initial application of 100 lbs of nitrogen. Using the received measurements, agricultural intelligence computer system 130 may identify a variability in the field. For example, agricultural intelligence computer system 130 may assume that the nutrient values within the field are uniform across locations. Thus, agricultural intelligence computer system 130 may collapse the plurality of measurements to one location and identify the variance of the plurality of measurements.

In an embodiment, agricultural intelligence computer system 130 imputes the uncertainty in a measurement based on the measurement value. For example, agricultural intelligence computer system 130 may receive only one measurement from a particular field instead of receiving a plurality of measurements across the field which can be collapsed to a single location to identify field variability. Agricultural intelligence computer system 130 may consult an uncertainty look up table which includes estimated uncertainty values for each measurement value of a particular nutrient. The uncertainty look up table may be populated through a plurality of field trials in which measurement uncertainty is computed, such as by using field variability. Each uncertainty value may be associated with a particular measurement value. As more trials are performed, a confidence in the uncertainty value for each measurement value increases. By using a plurality of field trials to identify probable uncertainty values for each measurement value, agricultural intelligence computer system 130 creates a method of identifying uncertainty that only requires a client computing device to provide a single measurement of nutrient content at a single point in the soil.

3.6 Assimilating Data Points

At step 712, a second digital model of nutrient content in the soil is generated and displayed based, at least in part, on the modeling uncertainty value and the measurement uncertainty value. For example, agricultural intelligence computer system 130 may inverse weigh the modeled property value by the modeling uncertainty to generate a weighted modeled property value. Agricultural intelligence computer system 130 may also inverse weight the measured property value by the measurement uncertainty to generate a weighted measured property value. The two weighted values may then be combined and multiplied by a covariance function to generate an assimilated model output.

In an embodiment, agricultural intelligence computer system 130 is programmed to compute the assimilated model output value using the following relationship:

$$E(\tilde{\eta}_t | Y_t) = \text{Cov}(\tilde{\eta}_t | Y_t) \left( n\tilde{H}^T \sum_{y_t}^{-1} \overline{Y}_t + \sum_{t}^{\tilde{-1}} \begin{pmatrix} \hat{\eta}_t^* \\ 0 \end{pmatrix} \right)$$

where $$\text{Cov}(\tilde{\eta}_t | Y_t) = \left( n\tilde{H}^T \sum_{y_t}^{-1} \tilde{H} + \sum_{t}^{\tilde{-1}} \right)^{-1}$$

where $E(\tilde{\eta}_t | Y_t)$ is the expected value of the assimilated nutrient content, $\tilde{\eta}$, at a particular time given received measurement data $Y_t$. The equation for the expected value of the assimilated property comprises a weighted measurement value term, $n\tilde{H}^T \Sigma_{y_t}^{-1} \overline{Y}_t$, where n is the number of measurements received, $\tilde{H}$ is a linear operator that maps the model output at multiple layers into corresponding measurement layers, $\Sigma_{y_t}$ is the estimated measurement error, and $\overline{Y}_t$ is the average of the measurement values for a particular soil level, location, and nutrient type. Each of the foregoing values or operators is represented in stored digital data or program instructions. The linear operator $\tilde{H}$ may be used to map modeled values to measured values when the values correspond to different soil layers. For example, if the nutrient content model identifies nutrient content in soil at layers of 0-3 cm, 3-6 cm, 6-9 cm, and 9-12 cm, but the measurements are taken for soil at layers of 0-6 cm, and 6-12 cm, the linear operator $\tilde{H}$ may transform the values of the measurements so that they correspond with the values of the modeled values.

The equation for the expected value of the assimilated nutrient content further comprises a weighted modeling value term, $$\sum_{t}^{\tilde{-1}} \begin{pmatrix} \hat{\eta}_t^* \\ 0 \end{pmatrix},$$

where $\tilde{\Sigma}_{y_t}$ is the estimated modeling error and $\hat{\eta}_t^*$ is the modeled nutrient value given default parameters and inputs. The default parameters and inputs are the expected values of the parameters and inputs with no perturbation. The equation for the expected value further comprises a covariance term, $\text{Cov}(\tilde{\eta}_t | Y_t)$, which takes the combination of weighted values and transforms the combination into non-weighted values.

In an embodiment, each of the uncertainty terms, $\Sigma_{y_t}$ and $\tilde{\Sigma}_{y_t}$ comprise covariance matrices. $\tilde{\Sigma}_{y_t}$ may be a covariance matrix generated from perturbed parameters and modeled values across one or more depths and/or nutrient types. For example, if measurements are received for two nutrients, $NO_3^-$ and $NH_4^+$, at depths that correspond to six different modeled depths, agricultural intelligence computer system 130 may construct a 12×12 covariance matrix for the uncertainty in the modeled nutrient content. $\Sigma_{y_t}$ may be a covariance matrix for measurement uncertainty based on received measurement values. For example, a correlation structure may be generated based on measurements at all locations and treatments for a particular field. By using values at all locations and treatments to create the correlation structure, agricultural intelligence computer system 130 is able to generate a correlation structure using a low number of measurements at each location and treatment. For example, if a farmer takes only one set of measurements at various locations in the field, a correlation structure which does not assume uniformity across locations limits the number of samples that can be used to assimilate at a given point to a single sample. The covariance matrix may then be scaled according to treatment and location specific marginal variances. For example, the correlation structure may be multiplied by a diagonal matrix comprising deviations from the mean at each location and treatment, in order to create a covariance matrix with location and treatment dependent terms. Thus, while the overall correlation structure may be assumed to be universal, the covariance matrix may assume that measured values are dependent on location and treatment.

The assimilated nutrient content value may be identified as a probable nutrient content in the soil. In an embodiment where moisture content and/or temperature measurements are assimilated into the model of nutrient content, the assimilated nutrient content value may be computed based on an assimilated moisture content and/or temperature value. In an embodiment, the assimilated data values comprise a distribution of assimilated values. For example, the uncertainties in the modeled value and the uncertainties in the measured value may be used to compute an overall uncertainty for the assimilated value. Using the uncertainty in the assimilated value, agricultural intelligence computer system 130 may identify a range of values for the nutrient content with corresponding probabilities. The range of values may be propagated in future computations and/or displayed on field manager computing device 104.

3.7 Model Calibration

In an embodiment, the assimilated property value is used to calibrate the nutrient content model for a particular property. Identifying the assimilated property value allows agricultural intelligence computer system 130 to run the nutrient content model for a particular point in time with the new value, thereby increasing the accuracy of the nutrient content model for future predictions. Agricultural intelligence computer system 130 may further increase the accuracy of the nutrient content model for future predictions by evaluating the parameters and inputs that went into the nutrient content model to reduce errors.

To calibrate the nutrient content model, agricultural intelligence computer system 130 may first identify parameters and inputs that lead to each value of the nutrient content model. For example, when identifying the modeling uncertainty, agricultural intelligence computer system 130 may perturb a plurality of parameters and/or inputs and compute a nutrient content value through the nutrient content model using each set of perturbed parameters and/or inputs. Agricultural intelligence computer system 130 may store each set of perturbed parameters with the result of running the nutrient content model using that set of parameters. The stored perturbed parameters may be ordered by the produced results, such that parameter sets which led to similar nutrient contents are easily identifiable.

After an assimilated property value is identified, agricultural intelligence computer system 130 may search through the stored sets of perturbed parameters for one or more sets of perturbed parameters and/or inputs that led to the same property value as the assimilated nutrient property value. Additionally, and/or alternatively agricultural intelligence computer system 130 may identify perturbations of parameters and/or inputs that produced results which were the closest to the assimilated property value. In an embodiment, agricultural intelligence computer system 130 selects a best set of perturbations of the parameters and/or inputs which led to the closest property value to the assimilated nutrient content value and uses the set of perturbations to run the nutrient content model. By using the perturbation set which led to the assimilated property value, agricultural intelligence computer system 130 removes a source of error which led to the modeled value differing from the measurement value. Thus, while using the assimilated property value to run the nutrient content model reduces errors in the results by minimizing the differences between the modeled content values and the measured content values at a particular time, calibrating the nutrient content model to a particular set of perturbations of parameters and/or inputs reduces errors in the results by removing the source of errors in estimates of perturbations and/or inputs.

In an embodiment, agricultural intelligence computer system 130 selects a set of inputs and/or parameters based on a plurality of assimilated property values. For example, agricultural intelligence computer system 130 may compute assimilated nutrient content values for a plurality of locations on a field, a plurality of depths of soil, a plurality of nutrient types, and/or a plurality of treatment types. Agricultural intelligence computer system 130 may select a set of perturbations which minimizes the squared differences between each modeled nutrient value and the corresponding assimilated nutrient value. Agricultural intelligence computer system 130 may also identify multiple sets of perturbations that led to either the assimilated nutrient content value or to a value within a particular range of the assimilated nutrient content value. For example, if agricultural intelligence computer system 130 generates a distribution of values for the assimilated nutrient content, agricultural intelligence computer system 130 may select perturbations which led to a value within the distribution. Using the multiple sets of perturbations, agricultural intelligence computer system 130 may compute a range of values for future nutrient contents in the soil, thereby propagating the uncertainty in the assimilated values to future nutrient values.

In an embodiment, agricultural intelligence computer system 130 stores the selected sets of parameters for each field in which an assimilated property value is computed. For example, agricultural intelligence computer system 130 may generate nutrient content models for a plurality of fields in a plurality of locations. Agricultural intelligence computer system 130 may also receive a plurality of data values identifying nutrient contents in soil for the fields in the plurality of locations. For each field, agricultural intelligence computer system 130 may perform the method described in FIG. 7 to generate an assimilated nutrient content value and calibrate the nutrient content model based on the assimilated nutrient content value. Agricultural intelligence computer system 130 may then store each set of perturbations along with information pertaining to a particular field, such as management practices, location, inputs, and number of measurements taken at the field.

Agricultural intelligence computer system 130 may use the stored perturbation data to generally strengthen the nutrient content model. For example, agricultural intelligence computer system 130 may identify parameters and/or inputs with selected perturbations that are frequently higher than the default value. Agricultural intelligence computer system 130 may then raise the value for the particular parameter based on the selected perturbations for the nutrient content model. Agricultural intelligence computer system 130 may also identify dependencies of parameters and/or input perturbation values on location, elevation, soil moisture, temperature, average precipitation, and/or one or more other inputs. For example, if selected perturbations of a particular parameter are generally higher than the default value in a plurality of fields in one geographical location but generally lower than the default value in a plurality of fields in a second geographical location, agricultural intelligence computer system 130 may store data identifying a location dependence on the value of the particular parameter.

4. Data Usage 4.1. Agronomic Models

In an embodiment, agricultural intelligence computer 130 uses the assimilated nutrient content value to generate an agronomic model. In an embodiment, an agronomic model is a data structure in memory of agricultural intelligence computer system 130 that contains location and crop information for one or more fields. An agronomic model may also contain agronomic factors which describe conditions which may affect the growth of one or more crops on a field. Additionally, an agronomic model may contain recommendations based on agronomic factors such as crop recommendations, watering recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

Lack of one or more nutrients may affect the potential yield of a crop. For example, nitrogen stress describes the effect of a crop's inability to receive an optimal amount of nitrogen on the growth of the crop. Each crop has a different optimal amount of nitrogen which defines a minimum amount of nitrogen below which the growth of the crop is adversely affected. Optimal amounts of nitrogen may change throughout the development cycle of the crop. Water stress likewise describes the effect of a crop's inability to receive an optimal amount of water on the growth of the crop and heat stress describes the effect of high temperatures on the growth of the crop. Based on received temperature, hydrology, and nutrient data, agricultural intelligence computer 130 may estimate the effects of nitrogen stress, heat stress, and water stress on the one or more crops. For example, nitrogen stress may lead to leaf destruction which lowers the leaf area index for a crop, thereby reducing the amount of sunlight received by the crop. Agricultural intelligence computer 130 may use digitally programmed logic and stored data indicating effects of specific amounts of nitrogen stress for a particular crop type to model changes in a crop's development. Based on the models of the crop as affected by either nitrogen stress, heat stress, water stress, or any combination thereof agricultural intelligence computer 130 may estimate a total yield for the crop.

In an embodiment, agricultural intelligence computer system 130 uses received input values and the assimilated nutrient content value to create an agronomic model in memory or in persistent storage in response to a request from field manager computing device 104 for an agronomic model. In other embodiments, agricultural intelligence computer system 130 receives a request from a third party for an agronomic model. For example, an insurance company may request an agronomic model for an insured customer's field to determine the risks associated with the crop planted by the customer. In another example, an application server may send a request to agricultural intelligence computer system 130 to create an agronomic model for a specific user's field. Alternatively, agricultural intelligence computer system 130 may generate agronomic models periodically. Agricultural intelligence computer system 130 may also generate agronomic models in response to receiving updated weather observations or in response to creating updated weather data, nutrient data, soil data, or other field data.

In an embodiment, agricultural intelligence computer system 130 sends agronomic models to field manager computing device 104. In other embodiments, agricultural intelligence computer 130 creates recommendations using agronomic models and sends the recommendations to field manager computing device 104. Agricultural intelligence computer system 130 may also store agronomic models in memory. Stored agronomic models may later be used to improve methods used by agricultural intelligence computer system 130 or to rate the various modeling methods.

4.2. Recommendations

In an embodiment, agricultural intelligence computer 130 creates one or more recommendations based on the assimilated nutrient content value. The one or more recommendations may include current watering recommendations, current nutrient application recommendations, and enhanced efficiency agrochemical application. For example, agricultural intelligence computer 130 may determine that nitrogen in the one or more fields will fall short of the nitrogen requirements for a crop on a certain date. In response, agricultural intelligence computer 130 may use the calibrated nutrient content model to model nitrogen applications prior to the certain date to determine when nitrogen would need to be added to the system to avoid the shortfall or to avoid the crop suffering damage from the shortfall. Agricultural intelligence computer 130 may create one or more recommendations for nitrogen application based on the determination. Additionally, agricultural intelligence computer 130 may determine if nitrogen lost to leaching, volatilization, or denitrification from the modeled nitrogen applications exceeds a specific threshold, and, in response to determining that the nitrogen loss exceeds the specific threshold, model applications of nitrogen inhibitors along with the nitrogen. Additionally, and/or alternatively, agricultural intelligence computer 130 may recommend an application of nitrogen inhibitors in response to a determination that nitrogen lost from the modeled nitrogen applications exceeds the specific threshold.

Recommendation module 152 may also create recommendations for water application based on a determination of fertility advisor module 136. For example, if fertility advisor module 136 determines that low moisture content in the soil is causing less of a nutrient to be available to the crop, recommendation module 152 may create a recommendation for water application in order to increase the nutrient availability for the crop. Fertility advisor module 136 may be configured to determine whether moisture content of the soil falls below a specific threshold. In response to the determination, fertility advisor module 136 may model the effects of adding water to the soil. In an embodiment, if fertility advisor module 136 determines that the addition of water increases the nutrient availability to the soil by more than a specific threshold, recommendation module 152 may create a recommendation for an application of water.

In an embodiment, fertility advisor module 136 sends the one or more recommendations to presentation layer 134. Presentation layer 134 may then send the one or more recommendations to field manager computing device 104. For example, field manager computing device 104 may send a request to agricultural intelligence computer system 130 for a planting recommendation for the next crop. Additionally, and/or alternatively, field manager computing device 104 may send a request to agricultural intelligence system 130 for a nutrient application recommendation. In response, presentation layer 134 may send a recommendation generated by recommendation module 152 to field manager computing device 104. The recommendation may be accompanied by nutrient availability graphs that depict nutrient availability for the crop based on an application of the recommendation.

In an embodiment, agricultural intelligence computer 130 sends the one or more recommendations to communication layer 132. Communication layer 132 may use the recommendations for water application, nutrient application, or enhanced efficiency agrochemical application to create application parameters for application controller 114. For example, agricultural intelligence computer 130 may create a recommendation for nutrient application based on estimated nutrient content values. In response to receiving the recommendation, communication layer 132 may use the nutrient availability data to create application parameters for a nutrient release valve that describe an amount of a nutrient to release on to the one or more fields. Presentation layer 134 may then send a notification to field manager computing device 104 indicating the nutrient availability data and requesting permission to apply the recommended nutrient to the one or more fields. In response to receiving permission to apply the recommended nutrient, communication layer 132 may send the application parameters to application controller 114. Application controller 114 may then implement the application parameters, such as releasing nitrogen onto the one or more fields or increasing the amount of water released to a specific crop.

5. Benefits of Certain Embodiments

Using the techniques described herein, a computer can deliver nutrient content data that would be otherwise unavailable. For example, the techniques herein can increase the precision of a nutrient content estimate using limited data, such as a single soil sample. The performance of the agricultural intelligence computing system is improved using the techniques described herein which decreases the number of computations necessary to compute an accurate nutrient content by performing a sensitivity analysis on particular parameters and/or inputs and calibrating a nutrient content model based on multiple assimilations. Additionally, the techniques described herein may be used to create application parameters for an application controller, thereby improving the performance of farming implements controlled by the application controller.

6. Extensions and Alternatives

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. A computer-implemented method comprising:
   storing, in digital memory of a computer system, a digital model of one or more properties of soil of one or more fields over a particular period of time;
   receiving, at the computer system over one or more networks from a client computing device, one or more digital measurement values specifying measurements of one or more properties of soil at a particular field of the one or more fields at a particular time within the particular period of time;
   identifying a modeled property value representing an estimate of the one or more properties of the soil at the particular field at the particular time;
   identifying one or more parameter uncertainties in one or more parameters of the digital model;
   perturbing the one or more parameters based on the one or more parameter uncertainties to produce one or more perturbed modeling results;
   identifying, based, at least in part, on the one or more perturbed modeling results, a modeling uncertainty value for the modeled property value of the digital model wherein the modeling uncertainty value represents a magnitude of error in the digital model;
   generating and displaying, based, at least in part, on the modeling uncertainty value and the one or more digital measurement values, an assimilated property value representing an improved estimate of the one or more properties of the soil at the particular field at the particular time.

2. The computer-implemented method of claim 1, further comprising:
   calibrating one or more parameters of the digital model to create a calibrated model of one or more properties of soil based on the assimilated property value.

3. The computer-implemented method of claim 1, further comprising:
   generating a plurality of combinations of a plurality of perturbed parameters from the one or more parameters and the one or more parameter uncertainties;
   for each combination of perturbed parameters, computing the one or more properties of the soil from the digital model with the perturbed parameters;
   identifying the modeling uncertainty value for the digital model based, at least in part, on the computed one or more properties of the soil for each combination of perturbed parameters.

4. The computer-implemented method of claim 3, further comprising:
   receiving, for a plurality of fields, field data comprising a plurality of values representing crop data, soil data, and weather data for the plurality of fields;
   computing, for each combination of perturbed parameters, for each field of the plurality of fields, the one or more properties of the soil from the digital model;
   computing, for each field of the plurality of fields, a sensitivity of the digital model to perturbations of the one or more parameters;
   computing, based, at least in part, on the sensitivity of the digital model to perturbations of the one or more parameters for each field of the plurality of fields and the received field data for the plurality of fields, a relationship between sensitivity of the digital model to perturbations of the one or more parameters and one or more values of the plurality of values representing crop data, soil data, and weather data for the plurality of fields;
   receiving, for the particular field, field data comprising a plurality of values representing crop data, soil data, and weather data for the particular field;
   computing, for the particular field, a particular sensitivity of the digital model to perturbations of the one or more parameters based, at least in part, on the field data and the relationship between sensitivity of the digital model and the one or more values of the plurality of values;
   computing, for the particular field, the modeling uncertainty value for the digital model based, at least in part, on the particular sensitivity of the digital model and the one or more parameter uncertainties.

5. The method of claim 1 further comprising:
   receiving, for the particular field, field data comprising a plurality of values representing crop data, soil data, and weather data for the particular field;
   creating one or more stabilizer recommendations based, at least in part, on the assimilated property value and the plurality of values representing crop data, soil data, and weather data for one or more fields;
   using a mobile device interface module, sending the one or more stabilizer recommendations to a field manager computing device.

6. The method of claim 1, further comprising:
   receiving, for the particular field, field data comprising a plurality of values representing crop data, soil data, and weather data for the particular field;
   creating one or more nutrient recommendations;
   generating instructions for an application controller based on the one or more nutrient recommendations and sending the instructions to the application controller;
   wherein the instructions cause the application controller to control an operating parameter of an agricultural vehicle to implement the one or more nutrient recommendations.

7. The method of claim 1, further comprising:
   receiving, for the particular field, field data comprising a plurality of values representing crop data, soil data, and weather data for the particular field;
   identifying one or more input uncertainties associated with one or more values of the plurality of values representing crop data, soil data, and weather data for the particular field;
   identifying the modeling uncertainty value for the digital model based, at least in part, on the one or more input uncertainties.

8. The method of claim 7, further comprising:
   wherein the weather data for the particular field includes radar based precipitation estimates;
   computing a precipitation estimate error for the radar based precipitation estimates;

identifying the one or more input uncertainties based, at least in part, on the precipitation estimate error.

9. The computer-implemented method of claim 1, further comprising:
identifying one or more modeled property values representing one or more estimates of the one or more properties of the soil at one or more locations across the particular field at the particular time;
identifying one or more modeling uncertainty values for the one or more modeled property values for the one or more locations across the particular field;
identifying, based, at least in part, on the one or more modeling uncertainty values for the one or more locations, one or more different modeling uncertainty values for one or more different locations;
generating and displaying, based, at least in part, on the one or more different modeling uncertainty values, the assimilated property value.

10. A data processing system comprising:
one or more processors;
a memory storing instructions which, when executed by the or more processors, cause:
storing a digital model of one or more properties of soil of one or more fields over a particular period of time;
receiving, from a client computing device, one or more digital measurement values specifying measurements of one or more properties of soil at a particular field of the one or more fields at a particular time within the particular period of time;
identifying a modeled property value representing an estimate of the one or more properties of the soil at the particular field at the particular time;
identifying one or more parameter uncertainties in one or more parameters of the digital model;
perturbing the one or more parameters based on the one or more parameter uncertainties to produce one or more perturbed modeling results;
identifying, based, at least in part, on the one or more perturbed modeling results, a modeling uncertainty value for the modeled property value of the digital model wherein the modeling uncertainty value represents a magnitude of error in the digital model;
generating and displaying, based, at least in part, on the modeling uncertainty value and the one or more digital measurement values, an assimilated property value representing an improved estimate of the one or more properties of the soil at the particular field at the particular time.

11. The data processing system of claim 10, wherein the instructions, when executed by the one or more processors, further cause:
calibrating one or more parameters of the digital model to create a calibrated model of one or more properties of soil based on the assimilated property value.

12. The data processing system of claim 10, wherein the instructions, when executed by the one or more processors, further cause:
generating a plurality of combinations of a plurality of perturbed parameters from the one or more parameters and the one or more parameter uncertainties;
for each combination of perturbed parameters, computing the one or more properties of the soil from the digital model with the perturbed parameters;
identifying the modeling uncertainty value for the digital model based, at least in part, on the computed one or more properties of the soil for each combination of perturbed parameters.

13. The data processing system of claim 12, wherein the instructions, when executed by the one or more processors, further cause:
receiving, for a plurality of fields, field data comprising a plurality of values representing crop data, soil data, and weather data for the plurality of fields;
computing, for each combination of perturbed parameters, for each field of the plurality of fields, the one or more properties of the soil from the digital model;
computing, for each field of the plurality of fields, a sensitivity of the digital model to perturbations of the one or more parameters;
computing, based, at least in part, on the sensitivity of the digital model to perturbations of the one or more parameters for each field of the plurality of fields and the received field data for the plurality of fields, a relationship between sensitivity of the digital model to perturbations of the one or more parameters and one or more values of the plurality of values representing crop data, soil data, and weather data for the plurality of fields;
receiving, for the particular field, field data comprising a plurality of values representing crop data, soil data, and weather data for the particular field;
computing, for the particular field, a particular sensitivity of the digital model to perturbations of the one or more parameters based, at least in part, on the field data and the relationship between sensitivity of the digital model and the one or more values of the plurality of values;
computing, for the particular field, the modeling uncertainty value for the digital model based, at least in part, on the particular sensitivity of the digital model and the one or more parameter uncertainties.

14. The data processing system of claim 10, wherein the instructions, when executed by the one or more processors, further cause:
receiving, for the particular field, field data comprising a plurality of values representing crop data, soil data, and weather data for the particular field;
creating one or more stabilizer recommendations based, at least in part, on the assimilated property value and the plurality of values representing crop data, soil data, and weather data for one or more fields;
using a mobile device interface module, sending the one or more stabilizer recommendations to a field manager computing device.

15. The data processing system of claim 10, wherein the instructions, when executed by the one or more processors, further cause:
receiving, for the particular field, field data comprising a plurality of values representing crop data, soil data, and weather data for the particular field;
creating one or more nutrient recommendations;
generating instructions for an application controller based on the one or more nutrient recommendations and sending the instructions to the application controller;
wherein the instructions cause the application controller to control an operating parameter of an agricultural vehicle to implement the one or more nutrient recommendations.

16. The data processing system of claim 10, wherein the instructions, when executed by the one or more processors, further cause:
receiving, for the particular field, field data comprising a plurality of values representing crop data, soil data, and weather data for the particular field;

identifying one or more input uncertainties associated with one or more values of the plurality of values representing crop data, soil data, and weather data for the particular field;

identifying the modeling uncertainty value for the digital model based, at least in part, on the one or more input uncertainties.

17. The data processing system of claim 16, wherein the instructions, when executed by the one or more processors, further cause:

wherein the weather data for the particular field includes radar based precipitation estimates;

computing a precipitation estimate error for the radar based precipitation estimates;

identifying the one or more input uncertainties based, at least in part, on the precipitation estimate error.

18. The data processing system of claim 10, wherein the instructions when executed by the one or more processors, further cause:

identifying one or more modeled property values representing one or more estimates of the one or more properties of the soil at one or more locations across the particular field at the particular time;

identifying one or more modeling uncertainty values for the one or more modeled property values for the one or more locations across the particular field;

identifying, based, at least in part, on the one or more modeling uncertainty values for the one or more locations, one or more different modeling uncertainty values for one or more different locations;

generating and displaying, based, at least in part, on the one or more different modeling uncertainty values, the assimilated property value.

19. A computer-implemented method comprising:

storing, in digital memory of a computer system, a digital model of one or more properties of soil of one or more fields over a particular period of time;

receiving, at the computer system over one or more networks from a client computing device, one or more digital measurement values specifying measurements of one or more properties of soil at a particular field of the one or more fields at a particular time within the particular period of time;

identifying one or more modeled property values representing one or more estimates of the one or more properties of the soil at one or more locations across the particular field at the particular time;

identifying one or more modeling uncertainty values for the one or more modeled property values for the one or more locations across the particular field, wherein the one or more modeling uncertainty values represent one or more magnitudes of errors in the digital model;

identifying, based, at least in part, on the one or more modeling uncertainty values for the one or more locations, one or more different modeling uncertainty values for one or more different locations;

generating and displaying, based, at least in part, on the one or more different modeling uncertainty values and the one or more digital measurement values, an assimilated property value representing an improved estimate of the one or more properties of the soil at the particular field at the particular time.

* * * * *